US010000778B2

(12) United States Patent
Medoff (10) Patent No.: US 10,000,778 B2
(45) Date of Patent: *Jun. 19, 2018

(54) CONVERSION SYSTEMS FOR BIOMASS

(71) Applicant: XYLECO, INC., Woburn, MA (US)

(72) Inventor: Marshall Medoff, Brookline, MA (US)

(73) Assignee: XYLECO, INC., Wakefield, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/481,472

(22) Filed: Sep. 9, 2014

(65) Prior Publication Data

US 2015/0031077 A1     Jan. 29, 2015

Related U.S. Application Data

(63) Continuation of application No. 13/759,601, filed on Feb. 5, 2013, now Pat. No. 8,852,907, which is a continuation of application No. 13/657,928, filed on Oct. 23, 2012, now Pat. No. 8,399,216, which is a continuation of application No. 12/374,549, filed as application No. PCT/US2007/074028 on Jul. 20, 2007, now Pat. No. 8,318,453.

(60) Provisional application No. 60/832,736, filed on Jul. 21, 2006.

(51) Int. Cl.
| | |
|---|---|
| *C07C 31/08* | (2006.01) |
| *C07G 1/00* | (2011.01) |
| *C12P 7/02* | (2006.01) |
| *C12P 7/08* | (2006.01) |
| *C12P 7/14* | (2006.01) |
| *C12P 7/06* | (2006.01) |
| *C12P 7/10* | (2006.01) |
| *C12P 5/00* | (2006.01) |
| *C12P 5/02* | (2006.01) |
| *C12P 7/64* | (2006.01) |
| *C12P 13/00* | (2006.01) |
| *C12P 19/34* | (2006.01) |
| *C12P 21/00* | (2006.01) |
| *C12P 33/00* | (2006.01) |

(52) U.S. Cl.
CPC ...... *C12P 7/14* (2013.01); *C12P 5/00* (2013.01); *C12P 5/023* (2013.01); *C12P 7/06* (2013.01); *C12P 7/10* (2013.01); *C12P 7/64* (2013.01); *C12P 13/001* (2013.01); *C12P 19/34* (2013.01); *C12P 21/00* (2013.01); *C12P 33/00* (2013.01); *Y02E 50/13* (2013.01); *Y02E 50/16* (2013.01); *Y02E 50/17* (2013.01); *Y02E 50/343* (2013.01); *Y02P 20/136* (2015.11); *Y02W 30/47* (2015.05)

(58) Field of Classification Search
CPC ...... C12M 23/58; C12M 33/14; C12M 43/02; C12M 43/08; C12M 21/04; C12M 21/12; C12M 23/52; C12M 45/06; C12P 21/00; C12P 7/20; C12P 7/6427; C12P 7/6463; C12P 7/6472; C12P 7/649; C12P 7/10; C12P 19/02; C12P 19/14; Y02E 50/343; Y02E 50/13; Y02E 50/16; C12N 1/12; C12N 9/2437; C12N 9/2445

USPC ....... 568/854; 530/412; 210/407; 435/286.6, 435/29, 3, 297.2, 165, 289.1, 294.1

IPC ............... C07K 1/141,1/14; C12N 1/121, 1/12, 9/02, 9/42; C12M 1/38, 1/02, 1/107, 1/12, 1/36; C12P 5/02, 7/10, 19/02, 19/14; C12Q 3/00; B01D 35/02

See application file for complete search history.

(56) References Cited

U.S. PATENT DOCUMENTS

| 97,787 | A | 12/1869 | Marshall et al. |
|---|---|---|---|
| 3,997,400 | A | 12/1976 | Heden |
| 4,237,226 | A | 12/1980 | Grethlein |
| 4,842,877 | A | 6/1989 | Tyson |
| 5,656,491 | A | 8/1997 | Cassani et al. |

(Continued)

FOREIGN PATENT DOCUMENTS

| DE | 3330094 | 3/1985 |
|---|---|---|
| DE | 19958142 | 2/2001 |

(Continued)

OTHER PUBLICATIONS

Athenstaedt et al. 1999 Identification and Characterization of Major Lipid Particle Proteins of the Yeast *Saccharomyces cerevisiae*. Journal of Bacteriology, vol. 181, No. 20, pp. 6441-6448.*

(Continued)

*Primary Examiner* — Louise Humphrey
*Assistant Examiner* — Kailash C Srivastava
(74) *Attorney, Agent, or Firm* — Leber IP Law; Celia H. Leber (57) ABSTRACT

The efficient production of ethanol from low-cost biomass (e.g., corn, sugar beets, sugar cane, switchgrass and/or paper) has become increasingly important in making ethanol competitive with gasoline and decreasing the United States' dependence on foreign oil. For example, to reduce the cost of transporting biomass to ethanol production facilities, mobile systems for producing ethanol from biomass are provided. Also provided are small-scale ethanol production facilities. For example, instead of transporting biomass to the production facility, the facility is transported to the biomass or is located nearby the source of the biomass. The ethanol production facilities or components thereof may be transported via land, water, or air. Production of other products, such as hydrocarbons, natural gas, hydrogen gas, plastics, polymers, and proteins, can also be made by the methods and facilities. Any product described herein can be made in finished form or un-finished form and moved, e.g., to a fixed facility, e.g., fixed production facility.

15 Claims, 2 Drawing Sheets

(56) References Cited

U.S. PATENT DOCUMENTS

| | | | |
|---|---|---|---|
| 5,970,846 A | 10/1999 | Roehr | |
| 6,878,212 B1 | 4/2005 | Pinatti | |
| 8,318,453 B2 * | 11/2012 | Medoff | 435/41 |
| 8,399,216 B1 * | 3/2013 | Medoff | 435/41 |
| 8,852,907 B2 * | 10/2014 | Medoff | 435/165 |
| 2004/0031932 A1 | 2/2004 | Belkin et al. | |
| 2008/0020437 A1 | 1/2008 | Savarese | |

FOREIGN PATENT DOCUMENTS

| | | |
|---|---|---|
| EP | 03075000 | 3/1989 |
| WO | WO 2005/06751 A2 * | 7/2005 |

OTHER PUBLICATIONS

Ratledge, C .1972. Microbial Oils and Fats: An Assessment of Their Commercial Potential. Progress in industrial Microbiology, vol. 16, pp. 119-206; M.J.Bull (Editor), Elsevier Scientific Publishing Company, Amsterdam, 1982.*

Bergman 1993. In "Dukes' Physiology of Domestic Animals" by Swenson & Reece, ed. (1993), http://arbl.cvmbs.colostate.edu/ Printed Jul. 27, 2017, 1993.*

Ingram et al., Genetic Engineering of Ethanol Production in *Escherichia coli*, Applied and Environmental Microbiology, vol. 53, pp. 2420-2425.

Misra, et al., "On Farm Composting Methods" FAO Land and Water Discussion Paper (FAO), No. 2, Rome Italy, 2003, 26 pages.

European Search Report, EP Application No. 07840465.4-1521/ 2049674 Jul. 12, 2010, 7 pages.

Stevens, R.W., "On the Stowage of Ships and their Cargoes," 1858, pp. 57-58, Section 190, Fermentation, Stevens, Plymouth.

Boggan, B., "Alchohol, Chemistry and You Sources and Uses of Ethyl Alcohol," pp. 1-5, 2008, Kennesaw State University.

NZ Examinaton Report, NZ Application No. 575045, dated Jun. 22, 2012, 2 pages.

AU Examination Report, AU Application No. 2007275036, dated Apr. 17, 2012, 5 pages.

Translation of KR Notice to Submit Response, Application No. 10-2000-007003526, dated Jan. 27, 2012, 3 pages.

Kape, H.E. et al., "Principles for Solid Manure Storage at Field Boundaries", Agricultural Professional Authorities, Jul. 19, 1994, 3 pages.

Summons to Attend Oral Proceedings, Corresponding EP Application No. 07840465.4, dated Jan. 14, 2016, 6 pages.

Extended European Search Report dated Jan. 9, 2018, issued in related EP Application No. 17191085.4 (4 pages).

\* cited by examiner

CONVERSION SYSTEMS FOR BIOMASS

CROSS REFERENCE TO RELATED APPLICATIONS

This application is a continuation application of U.S. patent application Ser. No. 13/759,601, filed Feb. 5, 2013, which is a continuation application of U.S. patent application Ser. No. 13/657,928, filed Oct. 23, 2012, now issued as U.S. Pat. No. 8,399,216, granted on Mar. 19, 2013, which is a continuation application of U.S. patent application Ser. No. 12/374,549, filed Jan. 21, 2009, now issued as U.S. Pat. No. 8,318,453, granted on Nov. 27, 2012, which is a national stage entry of PCT/US2007/74028, filed Jul. 20, 2007, which claims priority from U.S. Provisional Patent Application No. 60/832,735, filed on Jul. 21, 2006, the contents of which is incorporated herein by reference in its entirety.

TECHNICAL FIELD

The present invention relates to a system for producing energy (e.g., ethanol, hydrocarbons, gasoline, methane, natural gas, and biodiesel), electricity, nutrients (human and animal), pharmaceuticals (human and veterinary) (e.g., medicines, and drugs), fertilizer, or other co-products from biomass. In particular, the invention relates to mobile, portable, and modular facilities for producing energy (e.g., ethanol, hydrocarbons, gasoline, methane, natural gas, and biodiesel), electricity, nutrients (human and animal), pharmaceuticals (human and veterinary) (e.g., medicines, drugs), fertilizer, or other co-products, by fermentation or other process from biomass (e.g., crops, agricultural waste, and municipal solid waste).

BACKGROUND

Ethanol has a variety of uses, including as an industrial chemical and solvent, fuel additive, and straight liquid fuel. Ethanol is a clean burning fuel that can be produced from renewable sources such as crops (e.g., corn, and sugar cane), wood waste, agricultural waste, or other biomass. Ethanol not only reduces air emissions, but it also improves engine performance. Also, as a renewable fuel, ethanol reduces the United States' dependence on foreign fossil fuels. Recently, ethanol production in the United States has grown from 175 million gallons in 1980 to 3.4 billion gallons in 2004. There are currently 101 ethanol production facilities on-line in the U.S., and 30 more are under construction. Therefore, the production of ethanol in coming years is expected to increase.

The majority of ethanol made in the U.S. is derived from corn; however, ethanol can also be produced from other crops high in starches and sugars, such as grain sorghum, wheat, barley, potatoes, sugar cane, or sugar beets. The production of ethanol starts with breaking down the complex sugars (e.g., amylose, cellulose) found in these plants into simpler fermentable sugars (e.g., dextrose). This first step can be accomplished using enzymes, acid, water, and/or heat. Once the simpler sugars are obtained, yeast or other fermenting microorganisms are added to covert the sugar to ethanol. The ethanol is then removed from the fermentation by distillation. Water may be removed from the ethanol by dehydration, and the ethanol may be denatured to make it unfit for human consumption by adding a small amount of gasoline or other alcohol (e.g., methanol).

The production of ethanol as a fuel supplement has many benefits including boosting the economy, creating jobs, benefiting agriculture, aiding rural economic development, providing energy security and independence, reducing greenhouse gas emissions, and reducing emissions of other pollutants including carbon monoxide, particulate matter, oxides of nitrogen, and other ozone-forming pollutants.

Joseph DePardo in an article entitled "Outlook for Biomass Ethanol Production and Demand" (www.eai.doe.gov/oiaf/analysispaper/biomass.html) has said that the production of ethanol from corn is a mature technology that is not likely to see significant reductions in production costs. He hypothesizes that the ability to produce ethanol from other low cost biomass will be important to making ethanol competitive as a fuel additive. Therefore, a need remains for improving the production of ethanol from crops as well as other biomass including "non-virgin" biomass such as municipal solid waste.

SUMMARY OF THE INVENTION

The present invention provides for the production of energy (e.g., ethanol, hydrocarbons, gasoline, natural gas, methane, biodiesel, and hydrogen gas), electricity, plastics, polymers, nutrients (human and animal), proteins, biomolecules, pharmaceuticals (human and veterinary), fertilizer, or other products from biomass using a mobile or portable production facility or small-scale facility. The invention stems, at least in part, from the recognition that it may be more efficient, economical, and/or convenient to move the production facility or to have a small-scale facility nearby rather than moving the biomass used as the starting material in the process or the product such as ethanol produced by the facility. In certain embodiments, the inventive facilities allow the use of local supplies of biomass and other materials needed in the process such as water, electricity, natural gas, gasoline, and sewer. In the case of mobile facilities, the site may include certain infrastructure (e.g., a foundation (e.g., concrete slab)) for the facility, walls, roof, building, piping, wiring, sewer lines, gas lines, and lighting). The inventive facilities also allow for the use of biomass traditionally not thought of as useful for producing energy (e.g., ethanol, hydrocarbons, gasoline, natural gas, methane, biodiesel, and hydrogen gas), electricity, plastics, polymers, nutrients (human and animal), proteins, biomolecules, pharmaceuticals (human and veterinary), fertilizer, or other products, such as algae, aquatic plants, agricultural waste, and human waste. The inventive systems have personal, commercial, governmental, agricultural, and military applications.

In one aspect, the invention provides mobile production facilities for processing biomass to produce any of the desired products described herein. The mobile facilities of the invention are easily transported, or components of the facility are easily transportable. Transporting the production facility or components of the facility rather than the biomass starting material is particularly useful and economical given that many of the crops used to produce energy (e.g., bio-ethanol, gasoline, hydrogen, natural gas) or other desired products are seasonal. Therefore, a production facility only needs to be operational in the area when crops or other biomass is available for processing. After the processing is done, the facility or certain components of the facility can travel to another area with biomass available for conversion to a desired product. The inventive facilities or components thereof may be transported by water, air, land, or any combination thereof. The inventive facilities may include parts of the facility or infrastructure that is not transportable or mobile. For example, the inventive production facility or components thereof may be transportable on a boat, barge, ship, or other nautical vessel. Such facilities are particularly useful for producing ethanol or other products from aquatic biomass such as algae (e.g., *Sargassum*) or aquatic plants. These facilities are also useful in traveling on a body of water to different areas with biomass suitable for the production of the desired product (e.g., traveling on a river or on the ocean and docking at an area with suitable biomass for processing). The portable facilities or components thereof may also be transported on land. For example, the facility may be transported by a car, a truck, tractor trailer, and railroad car(s). Again, the land vehicle with the portable facility can travel to areas with biomass suitable for the production of the desired product. Finally, the facilities may be transported by air. The facility may be transported by plane, helicopter, and blimp. Air transportation of the facility allows for the use of biomass typically too far away from production facilities to be used. The facility may be on the plane, or the facility or components may be dropped from a plane or delivered by plane. The mobile facility is typically conveniently sized and organized to provide for easy transportation of the facility and/or its individual components. In the case of land transport, the transportation vehicles are typically able to travel roads and highways used by cars, trucks, and tractor trailers. In the case of sea transport, the facility or components are typically carried by a boat or barge which is moved by a boat. In the case of air transport, the facility or components is sized to fit in a plane (e.g., cargo plane) or helicopter.

The inventive mobile facilities or facilities constructed from mobile components may include any or all of the following apparatuses useful in producing the desired product (e.g., ethanol): pre-processing means for the biomass, mills, cookers, cooling containers, holding containers, fermenters, distillation apparatuses, columns, piping transfer containers, and mixing containers. In certain embodiments, the different stages of the production facilities are linked together efficiently so that a user can easily transfer materials from one stage of the production process to another. The facilities may also include any reagents needed in the production process including yeast or other microorganisms (including genetically engineered microorganisms), enzymes (e.g., amylase, and cellulase), acids (e.g., sulfuric acid, hydrochloric acid), bases (e.g., sodium hydroxide), chemical reagents, water, salts, molecular sieves, and columns. In certain embodiments, when ethanol is being produced, the facility includes denaturants such as gasoline or other alcohols for denaturing the ethanol. The inventive facilities can include all the necessary equipment and reagents conveniently stored in the facility making for easy use of the facility. In certain embodiments, the facility produces enough ethanol or other energy source to supply the energy needs of a factory, town, village, and island. In certain embodiments, the ethanol production facility produces less than 5 million gallons of ethanol per year. The facility may also optionally include any equipment mandated by international, federal, state, or local law including, for example, safety equipment necessary to prevent or handle spills, fires, or other emergencies.

As will be appreciated by one of skill in this art, the production facility may be assembled from various transportable components. These components may include pre-processing means for the biomass, mills, cookers, cooling containers, holding containers, fermenters, distillation apparatuses, columns, piping transfer containers, and mixing containers. In certain embodiments, the component comprises a combination of two or more of any of the above. The facility may include non-transportable components. These components of an ethanol production facility are designed for easy assembly of the working facility at the site. The components may be pre-fabricated. The components may be interchangeable and may provide for scalability of the facility. In certain cases, the components system allows the facility to be easily assembled and broken apart for ease of portability. The various components of the facility may be brought to the site using any combination of transport means (e.g., air, water, and land). In certain embodiments, the components are brought to a site with certain infrastructure which may include electricity, shelter, foundation, sewer, water, and natural gas lines. All or some of the components may be later disassembled and moved to a new site. In certain embodiments, particular components and/or the infrastructure may remain at the site to be optionally used again.

In some cases, the mobile production facility or components thereof are disposable so that after it has served its purpose a portion or all of the facility is abandoned temporarily or permanently. In other embodiments, the facility or components thereof are meant to be re-used and are therefore transported from place to place with suitable biomass. The facility may be completely self-sufficient requiring only the addition of biomass, or the facility may require other materials or utilities such as water, electricity, natural gas, gasoline, and sewer. For example, the ethanol or other energy produced by the mobile facility may be used to power a generator to supply electricity to the facility, or the ethanol or other energy source may be burned to provide the heat to break down the biomass in a cooker or to run a distillation. The ethanol or other energy may also be used to power the vehicle used to transport the facility or components thereof.

In another aspect, the invention also provides small-scale ethanol production facilities (e.g., producing less than 5 million gallons of ethanol). In certain embodiments, the inventive small-scale facilities produce less than 1 million gallons of ethanol. These small-scale facilities may be portable or components of the system may be portable as described above. These facilities may include any or all of the following apparatuses useful in producing bioethanol: pre-processing means for the biomass, mills, cookers, cooling containers, holding containers, fermenters, distillation apparatuses, columns, piping transfer containers, and mixing containers. In certain embodiments, the different stages of the production facilities are linked together efficiently so that a user can easily transfer materials from one stage of the ethanol production process to another. The facilities may also include any reagents needed in the ethanol production process including yeast or other microorganisms (including genetically engineered microorganisms), enzymes (e.g., amylase, and cellulase), acids (e.g., sulfuric acid, and hydrochloric acid), bases (e.g., sodium hydroxide), water, salts, molecular sieves, gasoline or other alcohols for denaturing the ethanol, and any other reagents. The inventive facilities can, e.g., include all the necessary equipment and reagents conveniently stored in the mobile facility making for easy use of the facility. In certain embodiments, the facility produces enough ethanol to supply the ethanol needs of a factory, town, village, and island. In certain embodiments, the facility produces less than 5 million gallons of ethanol per year. The facility may also optionally include any equipment mandated by international, federal, state, or local law including, for example, safety equipment necessary to prevent or handle spills, fires, or other emergencies. Other products as described herein may also be produced by the small-scale production facilities.

The present invention also provides processes for producing a desired product using an inventive facility. The process uses biomass from a local area in an inventive production facility to produce the desired product locally. The locally produced product (e.g., ethanol, gasoline, natural gas, hydrogen gas, and hydrocarbons) is then preferably used locally to avoid the cost of the transporting both the biomass and the final product. Preferably, a local water source is used in the production process. Other reagents needed for the process may be provided by the facility or provided locally. The waste or co-products from the production process, e.g., the distillers grain, can be used locally as a highly nutritious livestock feed or as a fertilizer. Other waste products or co-products from the process such as biomolecules, carbohydrates, protein, and polymers may also be packaged, used, and/or sold.

The mobile component-based ethanol production facilities and small-scale production facilities complement larger-scale ethanol production facilities (i.e., facilities that produce over 10-20 million gallons of ethanol per year). In some cases, the inventive facilities may eliminate the need for large-scale ethanol production facilities in some areas. The portable nature of certain systems works especially well given the cyclical nature of crops and other biomass in various geographic areas. These inventive facilities also allow for the economical production of ethanol from low cost biomass, which will aid making ethanol a competitive fuel additive. In certain embodiments, the inventive system uses biomass that is not corn, sugarcane, or sugarbeet, or includes a small portion of these crops.

In one aspect, the invention features a facility for producing ethanol from biomass. Such a facility includes at least one component that is portable.

In some embodiments, the component performs at least one step in the process of converting biomass to ethanol. For example, the component can pre-processes the biomass, ferment the biomass, or purify ethanol produced from the biomass.

In some embodiments, the facility is capable of only producing less than about 1 million gallons of ethanol per year, or less than about 5 million gallons of ethanol per year.

In some instances, the facility includes at least two portable components.

In another aspect, the invention features a portable facility for producing ethanol from biomass.

In another aspect, the invention features a portable facility for producing ethanol from biomass. Such a facility includes a means for transporting the facility and a fermenter for converting sugars derived from biomass into ethanol.

For example, the facility can be transported by land. For example, the facility can be transported by railroad.

For example, the facility can be transported by water, such as by using a boat, barge or other nautical vessel.

For example, the facility can be transported by air, such as by using an airplane or helicopter.

For example, more than one mode of transportation can be used. For example, any one or more of air, land or nautical modes may be utilized. For example, train in combination with barge or boat, or blimp in combination with train.

For example, the facility can further include a means for converting complex sugars of biomass into simpler, more fermentable sugars.

For example, the facility can also include a means for purifying the ethanol produced in the fermenter, such as one or more distillation columns.

In another aspect, the invention features a portable facility for producing ethanol from biomass that includes a means for transporting the facility, a mill for grinding the biomass, a cooker for liquefying the biomass, a fermenter for converting sugars derived from biomass into ethanol and a distillation apparatus.

In another aspect, the invention features a method of producing ethanol from biomass that includes providing biomass; providing a portable ethanol production facility; and producing ethanol from the biomass using the portable ethanol production facility.

In another aspect, the invention features methods of producing ethanol from biomass, e.g., one or more cellulosic and/or lignocellulosic materials (e.g., switchgrass and/or paper), that include producing ethanol from biomass at a first site with a reactor or a converter, e.g., a fermenter; transporting the reactor or converter to a second site; and producing ethanol from biomass at the second site with the reactor or converter.

For example, the biomass can be or can include any cellulosic or lignocellulosic material, such as corn, sugar cane, sugar beets, trees, shrubs, grasses, phytoplankton, zooplankton, algae, macroalgae, seaweed, corn husks, bushes, lumber, wood waste, pulp, cotton, wool, linen, paper, newspapers, corrugated containers, mixed paper, computer printouts, white office paper, printing plant scraps, leaves, twigs, grass, plant cuttings, branches, trees, vines, sewage, agricultural waste. Mixtures of any of these can also be utilized.

For example, transporting can be performed with a nautical vessel, e.g., a boat, a barge, a ship, dock or a floating platform. For example, transporting can be performed with a land vehicle, such as a car, truck, tractor trailer or train. For example, transporting can be performed with an airborne vehicle, such as a plane, helicopter or blimp.

In some embodiments, transporting is performed by more than a single mode, such as by a land vehicle and a water vehicle.

In some embodiments, the producing is performed while transporting.

In some embodiments, the system uses fixed resources, such as piping and/or electricity a given site.

In some embodiments, the reactor or converter forms part of a system and the system also includes a component such as cutters, shearing devices, measuring devices, flow devices, mills, mixers, pumps, wiring, cookers, heaters, coolers, aerators, containers, holding containers, distillation columns, piping, or mixtures of these.

Spacing between a first site and a second site can be small or relatively large. For example, the sites can be physically beside one another. For example, the ethanol can be produced while the system is being carried by a moving train.

In other embodiments, the first site and second site are spaced apart by a distance of about 25 miles or more, e.g., about 50 miles or more, about 75 miles or more, about 100 miles or more, about 150 miles or more, about 250 or more miles, or even about 500 miles or more.

In some embodiments, producing ethanol from biomass at the first and/or second site includes hydrolyzing the biomass, and then fermenting the biomass.

The methods can further include, e.g., transporting the system to a third site, and then producing ethanol at the third site. The methods can include also a fourth, fifth, sixth, seventh, eighth or more sites. Producing can occur at any number of these sites.

In some embodiments, prior to producing ethanol from biomass at the first and/or second site with the system, the system is assembled.

For example, the producing ethanol from biomass can include contacting the biomass with one or more microorganisms, such as a one or more species of yeast and/or bacteria, disposed in the fermenter. Combinations of different organisms may be used, e.g., combinations of yeast and bacteria or different species of yeast or bacteria.

For example, the one or more microorganisms can include one or more genetically engineered bacteria.

In another aspect, the invention features methods of producing energy from biomass that include producing a first energy source from biomass at a first site with a reactor or a converter; transporting the reactor or a converter to a second site; and producing a second energy source from biomass at the second site with the reactor or a converter.

In some embodiments, the first and second energy sources are the same.

For example, the energy source can be an alcohol, such as ethanol or n-butanol, gasoline, hydrocarbons, hydrogen, natural gas, biodiesel, electricity or mixtures of any of these.

In specific embodiments, the energy source is or includes an alcohol, such as ethanol.

In another aspect, the invention features methods of producing products from biomass that include producing a first product from biomass at a first site with a reactor or a converter; transporting the system to a second site; and producing a second product from biomass at the second site with the reactor or a converter.

In some embodiments, product of products can be made in a mobile facility, and then finished in a fixed facility, e.g., fixed production facility. For example, the un-finished product or products can be transported by a vehicle, e.g., a train and/or a ship, or another conveyance method, such as pipes. Combinations of these conveyance methods can be utilized.

In some embodiments, the first and second products are the same.

In some embodiments, the first or second products include ethanol and/or n-butanol.

For example, product can be ethanol, n-butanol, hydrocarbons, gasoline, natural gas, methane, biodiesel, hydrogen, electricity, polymers, nutrients, proteins, biomolecules, pharmaceuticals, pharmaceutical products, fertilizer or mixtures of any of these.

In some embodiments, the first or second products include one or more biomolecules. For example, the biomolecule can be a nucleic acid, a protein, a lipid, a steroid, a natural product, a metabolic product, a nucleotide, a fat, an amino acid, a peptide or mixtures of any of these.

In another aspect, the invention features methods of producing products from biomass, e.g., cellulosic or lignocellulosic materials, the include producing a first product from biomass at a first site with a reactor, the first site being located on a body of water; transporting the reactor to a second site also on the body of water; and producing a second product from biomass at the second site with the reactor. In such aspects, the biomass can obtained from the body of water.

For example, the biomass can be plankton, aquatic plants, algae, seaweed or mixtures of these.

In another aspect, the invention features methods of producing products from biomass that include producing a first product from biomass at a first site with a reactor or converter; transporting the reactor or converter by a first mode to a second site; producing a second product from biomass at the second site with the reactor or converter; and transporting the reactor or converter by a second mode different than the first mode to a third site.

Definitions

"Bioethanol": The term "bioethanol" refers to ethanol produced partially or entirely from biomass. In certain embodiments, bioethanol is produced by fermentation of sugars derived from biomass. The term bioethanol is used interchangeably herein with the term ethanol.

"Biomass": The term "biomass" refers to any material or combination of materials that can be used in the production system to produce energy (e.g., ethanol, hydrocarbons, gasoline, natural gas, methane, biodiesel, and hydrogen gas), electricity, plastics, polymers, nutrients (human and animal), proteins, biomolecules, pharmaceuticals (human and veterinary; e.g., drugs and medicines), fertilizer, or other products. In certain embodiments, sugars or other organic compounds from the biomass are converted into ethanol (e.g., by fermentation). Exemplary biomass includes crops (e.g., corn, sugar cane, sugar beets), trees, shrubs, grasses, plankton (e.g., phytoplankton, zooplankton, bacterioplankton), algae, macroalgae (e.g., species from the genus *Sargassum*), seaweed, agricultural waste (e.g., branches, corn husks, bushes, and weeds), synthetic materials, synthetic plastics, industrial waste, recycled waster, municipal solid waste, synthetic waste, human waste, animal waste, commercial organics (e.g., beverage industry waste, cheese, whey, dairy waste, food processing waste, lumber and industrial wood waste, pulp and paper facility waste, restaurant waste, fabrics, cotton, wool, and linen), construction and demolition debris, waste paper (e.g., old newspapers, old corrugated containers, mixed paper, pulp substitutes, computer printouts, white office paper, and printing plant scraps), yard waste (e.g., leaves, twigs, grass, plant cuttings, branches, trees, and vines). Biomass includes both virgin biomass and non-virgin biomass.

"Biomolecule": The term "biomolecule" refers to any chemical compound that can be produced by a cell or organism. In certain embodiments, the cell is wild type and has not been genetically engineered by the hand of man. In other embodiments, the cell has been altered by the hand of man. Exemplary biomolecules include nucleic acids, proteins, lipids, steroids, natural products, metabolic products, nucleotides, nucleosides, fats, amino acids, and peptides.

"Components": The term "component" refers to any part of a biomass conversion facility. The component may be of any size or shape. It may include one or multiple pieces of equipment used in the energy production or biomass conversion process. In certain embodiments, the component includes several pieces of equipment. It may optionally include piping or wiring and may optionally include hook-ups so that it can be connected with other components or infrastructure at the site. In certain embodiments, the component is transportable by air, water, or land. Exemplary components comprise one or more of the following: pre-processing means for the biomass, mills, mixers, pumps, wiring, cookers, heating means, cooling means, aeration means, cooling containers, holding containers, fermenters, distillation apparatuses, columns, piping, transfer containers, and mixing containers. In certain embodiments, the components are for the modular assembly of an ethanol production facility.

"Dehydration": The term "dehydration" refers to removing water from a material. In certain embodiments, dehydration refers to removing water from the ethanol produced by the system. The resulting ethanol may be free of ethanol, or 1, 2, 3, 4, or 5% water may remain in the ethanol. In certain embodiments, the ethanol after dehydration includes less than 1% water. The ethanol may be dehydrated using any means known in the art including distillation, azeotroping, or using molecular sieves.

"Denatured ethanol": The term "denatured alcohol" refers to ethanol that has been mixed with another material to make it unfit for human consumption. In most jurisdictions, the sale of ethanol, as a pure substance or in the form of alcoholic beverages, is heavily taxed. In order to relieve non-beverage industries of this tax burden, governments specify formulations for denatured alcohol, which consists of ethanol blended with various additives to render it unfit for human consumption. These additives, also known as denaturants, are either toxic and/or have an unpleasant taste or odor. Denatured ethanol formulations intended for a particular use (e.g., use as a fuel additive) contain denaturants chosen so as not to interfere with that use.

"Distillation": The term "distillation" refers to a process of purifying the ethanol from the fermented mash. The distillation process typically involves a change of state from a liquid to a gas and subsequent condensation as a means of purification.

"Energy": The term "energy" includes any energy source that can be produced from biomass. The energy produced from biomass is typically organic compounds. The energy can be burned to produce heat which can be used to produce electricity or power a vehicle for example. In certain embodiments, the energy is ethanol. In other embodiments, the energy is alcohol. In other embodiments, the energy is hydrocarbons. In certain embodiments, the energy is fats. In certain embodiments, the energy is fatty acids. In other embodiments, the energy is acetic acid. In other embodiments, the energy is gasoline. In certain embodiments, the energy is a mixture of organic compounds. In certain embodiments, the energy is natural gas. In certain embodiments, the energy is hydrogen gas. In certain embodiments, the energy is methane gas. In certain embodiments, the energy is biodiesel. In certain embodiments, the energy is electricity.

"Ethanol": The term "ethanol" refers to the chemical compound, $CH_3CH_2OH$. Ethanol is also referred to as grain alcohol. Ethanol is a flammable, tasteless, colorless, mildly toxic chemical compounds with a distinctive odor. The term ethanol may refer to any degree of purity of ethanol. In certain embodiments, the ethanol is at least 50%, 60%, 70%, 80%, 90%, 95%, 98%, or 99% pure. In some cases, the ethanol is 100% pure. In other cases, the ethanol is denatured with 1-10% or 2-5% other solvents (e.g., methanol, isopropanol, gasoline, hexanes, pentane) to make it unfit for human consumption. In certain embodiments, the ethanol is mixed with water. In other embodiments, the ethanol is anhydrous (e.g., after a dehydration step).

"Fermentation": The term "fermentation" refers to the process of converting sugars to ethanol or any other desired products including energy (e.g., hydrocarbons, gasoline, natural gas, methane, biodiesel, and hydrogen gas), electricity, plastics, polymers, nutrients (human and animal), proteins, biomolecules, pharmaceuticals (human and veterinary; e.g., drugs and medicines), and fertilizer. In certain embodiments, the term fermentation refers to the process of making organic molecules useful as an energy source from biomass. Fermentation is typically performed by microorganisms such as bacteria or yeast. The fermentation process for ethanol is typically performed in an oxygen-deficient atmosphere to prevent the further oxidation of the desired ethanol to acetic acid.

As defined herein, a "fermentor, reactor or a converter" is a device that is capable of holding at least about 1,000 gallons of material, such as a cellulosic and/or lignocellulosic material, a microorganism and a solvent, such as water. In some embodiments, the fermenter, reactor or converter is capable of holding greater than about 2,000 gallons of material, greater than about 2,500 gallons, greater than about 5,000 gallons, greater than about 10,000 gallons, greater than about 25,000 gallons, greater than about 50,000 gallons, or even greater than about 100,000 gallons.

All publications, patent applications, patents, and other references mentioned herein are incorporated by reference in their entirety for all that they contain.

Other features and advantages of the invention will be apparent from the following detailed description, and from the claims.

DETAILED DESCRIPTION

Described herein are mobile and/or small-scale (e.g., less than 1-5 million gallons per year) systems for producing energy (e.g., ethanol, hydrocarbons, gasoline, natural gas, methane, biodiesel, and hydrogen gas), electricity, plastics, polymers, nutrients (human and animal), proteins, biomolecules, pharmaceuticals (human and veterinary; e.g., drugs and medicines), fertilizer, or other products including processes, facilities, and components of the facility for producing the desired product, from biomass. The systems eliminate or at least reduce the need for transporting the starting material biomass, which can be, e.g., of a low bulk density, to a stationary large-scale production facility. It also may reduce the need to transport the desired product produced by the mobile facility a long distance to its end user or a distribution facility. The system for producing the desired product allows for the processing of biomass that ordinarily would not be economically suitable for conversion to energy (e.g., ethanol, hydrocarbons, gasoline, natural gas, methane, biodiesel, and hydrogen gas), electricity, plastics, polymers, nutrients (human and animal), proteins, biomolecules, pharmaceuticals (human and veterinary; e.g., drugs and medicines), fertilizer, or other products due to transportation, processing, or other costs. The system makes the production of energy (e.g., ethanol, hydrocarbons, gasoline, natural gas, methane, biodiesel, and hydrogen gas), electricity, plastics, polymers, nutrients (human and animal), proteins, biomolecules, pharmaceuticals (human and veterinary; e.g., drugs and medicines), fertilizer, or other products more economical by reducing the costs, particularly the transportation costs, of producing the desired product.

Production facilities that are configured in such a way that it or its various components can be easily transported by land, sea, air, or a combination thereof. In certain embodiments, the materials and equipment need to produce desired product from biomass are compactly organized so that it or its components can be transported by a car, truck, tractor trailer, railroad, boat, barge, airplane, helicopter, or combination thereof. In certain embodiments, the facility or its components may be limited in size depending on how the facility or its components are transported. For example, a facility or component being transported by tractor trailer will need to fit on the bed of a truck or trailer for transport.

Figure 1:
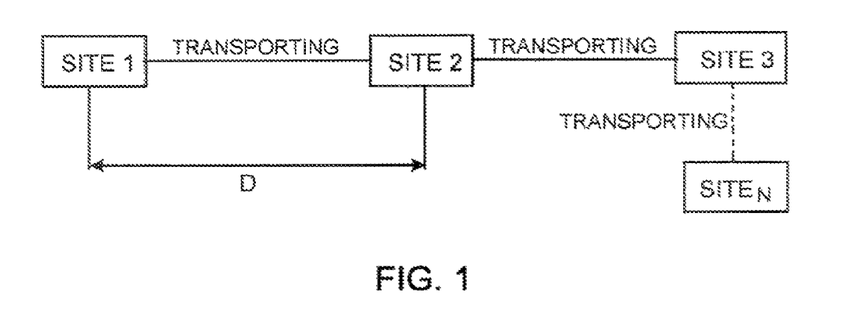
FIG. 1 is a block diagram that schematically illustrates methods of producing various products, such as ethanol or n-butanol.

Referring to FIG. 1, methods of producing products, such as ethanol or n-butanol, from biomass, e.g., cellulosic or lignocellulosic material, include producing a first product at a first site with a system that includes a reactor or converter, e.g., a fermenter. The system is transported to a second site, and then a second product is produced from biomass at the second site with the system.

Any number of sites may be utilized. For example, the number of sites can be 2, 3, 4, 5, 6, or more, e.g., 10, 20, 30, 50, 100 or more, e.g., 1000.

For example, a site may form part of a complex or a campus, and portions of the complex or campus may be joined by various manufacturing infrastructure, such as rail.

Spacing between a first site and a second site can be relatively small or relatively large. For example, the sites can be physically beside each other. For example, the system can be carried by a moving train and producing ethanol while moving.

In other embodiments, the first site and second site are spaced apart by a distance of about 10 miles or more, e.g., about 25 miles or more, about 35 or more, about 65 miles or more, about 85 miles or more, about 100 or more, about 200 miles or more, about 300 or more, or even about 500 miles or more.

In some embodiments, the fermentor, reactor or converter can hold between about 1,000 gallons and about 100,000 gallons of material, e.g., between about 2,500 gallons and about 100,000 gallons, or between about 5,000 gallons and about 75,000 gallons.

In certain embodiments, the mobile systems or one or more of its components for producing the desired product is transported by land. When the mobile facility or its components is transported by roads, it preferably complies with all applicable laws governing the roads of that country, state, province, county, or city. In the U.S., facilities transported by land using highways and roads may comply with all federal, state, and local laws and regulations. In certain embodiments, the mobile facility being transported by a tractor trailer is no larger than 8 feet 6 inches wide and no longer than 57 feet in length. In certain embodiments, the facility is no wider than 8 feet 6 inches and no longer than 53 feet. In certain embodiments, the facility is no wider than 8 feet 6 inches and no longer than 48 feet. In certain embodiments, the facility is no wider than 8 feet 6 inches and no longer than 20-24 feet in length. The height of the vehicle may vary depending on the obstacles on the road the facility is being transported via. However, typically the facility is less than 15 feet in height. In certain embodiments, it is less than 14 feet in height. In certain embodiments, the facility is transported by a double tractor trailer in which case the total length for the combination is no greater than 75 feet. In certain embodiments, the total length of the double is no greater than 65 feet. In certain embodiments, the gross combination weight of the vehicle with the mobile facility or one or more of its component(s) is no greater than 80,000 pounds. In certain embodiments, the facility or a component thereof fits into a standard container used for shipping by tractor trailer. As would be appreciated by one of skill in this art, the components of the facility may be transported by more than one land vehicle or may be transported by a land vehicle and a combination of land, water, and air vehicles. In certain embodiments, components that are not suitable for transport by water or air are transported by land. In certain embodiments, components for which water and/or air transportation are not economical are transported by land. However, it is appreciated that in certain embodiments land transportation of the facility or its components is not feasible or is not possible (e.g., due to lack of passable roads).

In certain embodiments, the mobile production facility or some of its components are small enough to be transported by a car, sport utility vehicle (SUV), or pickup truck. In certain embodiments, the facility or its components are transported on a trailer pulled by a car, SUV, or pickup truck.

The mobile facility or its various components can also transportable by railroad. In certain embodiments, the facility to be transported by rail is no wider than 14 feet. In other embodiments, the facility is no wider than 13 feet 6 inches. In still other embodiments, the facility is no wider than 13 feet. In certain embodiments, the facility is no wider than 12 feet 6 inches. The width clearance of the facility including its outer container will depend on the railways being used to transport the facility. In certain embodiments, the minimum width of 12 feet 6 inches or 13 feet is used to accommodate all railways the facility could possibly travel along. The length of the facility is no longer than 60 feet. In embodiments, the length of the facility is less than 60 feet. In certain embodiments, the length is approximately 58 feet. In other embodiments, the length is approximately 59 feet, approximately 57 feet, or approximately 56 feet. The height of the facility is typically less than 23 feet. In certain embodiments, the height is less than 22 feet. In other embodiments, the height is less than 21 feet. In certain embodiments, the height is less than 20 feet. In certain embodiments, the facility or a component thereof fits into a standard container used for shipping by railroad. In yet other embodiments, the height is less than 19 feet. The weight of the facility typically does not exceed 200,000 pounds. In certain embodiments, when a larger mobile production facility is needed, the facility is transported using more than one railroad car where each railroad car includes a component. These components are then assembled into an operational facility at the desired site. In certain embodiments, the facility is assembled on a rail road track, set of tracks, or spur. In certain embodiments, the facility comprises 1-10 railroad cars. In certain embodiments, the facility comprises 1-5 railroad cars. In certain embodiments, each step or a combination of steps of the process of producing ethanol is performed in a separate car. In certain embodiments, the equipment for performing one or more steps is combined into one car. Various components of the facility may also be brought to the site for assembly by other land transportation, air transportation, or water transportation.

Any combination of transporting modes can be utilized. For example, the systems can be transported by land, and then by water, or by air and then by land.

For example, the products such as ethanol can be produced during transportation or after transportation.

When the facility or its components are transported by water, the facility is optionally within the allowed limits of the vessel transporting the facility or component(s). These limits include length, width, height, and weight limits of the vessel transporting the facility. As will be appreciated by one of skill in this art, the size of the facility will greatly depend on the size of the vessel transporting the facility or its component(s). Larger ships and barges can transport a much larger ethanol production facilities than smaller boats. When the facility or its component(s) are transported by water, the facility may be assembled on a barge, dock, wharf, platform, derek, rig, sand bar, and island. In certain embodiments, the facility or a component thereof fits into a standard container used for shipping by water. In certain embodiments, the facility is assembled on a flotation device. Various components of the facility may be brought to the site for the facility by land or air as well as by water. Facilities on the water or close to the water facilitate the use of aquatic biomass such as plankton, algae, and aquatic plants in the production of the desired product.

Similarly, when the facility is transported by air, the facility or its component(s) are optionally within the allowed limits of the aircraft transporting the facility. These limits include length, width, height, and weight limits of the aircraft transporting the facility. In certain embodiments, the aircraft is an airplane. The airplane may be a propeller driven plane, a jet, a cargo plane, a military plane, and a commercial airliner. In certain embodiments, the aircraft is a helicopter. In certain embodiments, the aircraft will transport the facility or the component(s) hanging from the aircraft. In certain embodiments, the facility or a component thereof fits into a standard container used for shipping by air. The facility or component may land with the aircraft and be unloaded from the aircraft for use or the facility or component may be used while on board the aircraft. In certain embodiments, the facility or component is dropped from the air to the site where it is to be used. In certain embodiments, the facility or component includes parachutes or other landing device for a safe landing of the facility. The facility may also include a floatation device for a water landing. In certain embodiments, the facility or a component thereof includes a means for absorbing the impact of the landing. In certain embodiments, the facility or components is later moved by land, air, or water to a new site. In other embodiments, the facility or components are not moved and may be abandoned temporarily or permanently. Various other components of an facility may be transported by land or water as well as air. The components may be assembled into an operational facility at an airport, landing strip, drop site, or any other land or water site.

In certain embodiments, the facilities or any of its components are capable of being transported by any combination of air, land, and/or water transport. In certain embodiments, the facility or its components are transported by all three. In other embodiments, the facility or its components are transported by land and water. In certain embodiment, the facility or its components are transported by land and air. In other embodiments, the facility or its components are transported by air and water. In these cases, the vehicle transporting the facility or any of its components preferably meets the requirements (e.g., length, width, height, and weight) of the mode of transportation being used. Given that the ethanol, hydrocarbons, natural gas, or gasoline being produced are flammable, any applicable safety laws, rules, or regulations are preferably followed regarding the transport and production of a flammable liquids or gases. In certain embodiments, equipment for handling spills, fires, and explosions is incorporated into the facility.

In certain embodiments, the facilities include at least one portable component used in the production of energy (e.g., ethanol, hydrocarbons, gasoline, natural gas, methane, biodiesel, and hydrogen gas), electricity, plastics, polymers, nutrients (human and animal), proteins, biomolecules, pharmaceuticals (human and veterinary; e.g., drugs and medicines), fertilizer, or other products from biomass. The assembled facility as well as any components of the facility are considered to be within the scope of the disclosure. A component-based facility allows for easy assembly of the facility, interchangeability, scalability, and pre-fabrication of the components. Breaking the facility into various components also facilitates the mobility aspect of the facility. In certain embodiments, the facility is divided into two, three, four, five, six, seven, eight, nine, ten, or more components. Each components may include one or more pieces of equipment with the necessary wiring, piping, drains, control systems, heating and cooling means, stands, coupling devices, and outlets. In certain embodiments, the component include walls, roof, flooring, or other infrastructure for the component itself, other components, or the entire facility. In certain embodiments, the component includes a contained for easy transport of the component. The container may be used in the production process (e.g., as a mixing container or other vat). The sides, bottom, or top of the container may be used as the walls, floor, or roof of the shelter housing the facility or components thereof.

In certain embodiments, each step of the production process is performed in a separate component. That is, all the equipment for a step in the process is included in the component. The various steps and equipment useful in the production of bioethanol from biomass are described herein. In other embodiments, a step may require equipment from one or more components. In other embodiments, more than one step of the production process is included in a component. One or more components of the facility are assembled to produce an operable facility. The components are typically assembled at a site prepared for the installation. However, in certain embodiments, there is no preparation or infrastructure at the site. Instead, the facility or components are self-supporting. In certain embodiments, the components are assembled using a crane, fork lift, truck, or other moving device, which is optionally included in the system. In other embodiments, the components are assembled using only human labor. Tools may be used in the assembly of the facility. The site may include all the necessary infrastructure to make the facility operational. Infrastructure may include walls, roof, foundation, floor, electricity, wiring, piping, sewer, water, and natural gas. In certain embodiments, the infrastructure is not mobile and is stationary. When the facility or any of its components are moved, the infrastructure may left behind to potentially be used again the future. In certain embodiments, the infrastructure is used to assemble an production facility every month, every season, every year, or any time sufficient biomass is available at the site to supply the facility.

Ethanol production facilities that are smaller in scale than traditional ethanol production facilities. Typically, ethanol production facilities produce greater than 10-20 million gallons of ethanol per year with some facilities exceeding 50 million gallons of ethanol per year. The facilities produce less than 5 million gallons of ethanol or other energy source per year. In certain embodiments, the facility produces less than 1 million gallons of ethanol or other energy source per year. In certain embodiments, the facility produces less than 0.5 million gallons of ethanol or other energy source per year. In certain embodiments, the facility produces less than 0.1 million gallons of ethanol or other energy source per year. In certain embodiments, the facility produces less than 0.01 million gallons of ethanol or other energy source per year. In certain embodiments, the facility produces less than 0.001 million gallons of ethanol or other energy source per year. These facilities may be mobile or include mobile components as described herein. In certain embodiments, the facility is stationary. The amount of energy produced by a facility is sufficient to meet the demands of a factory, military base, small town, rural village, county, farm, and island. The small size of the facility allows for numerous facilities to be placed in a geographic region. For example, a facility may be placed in any areas where there is sufficient biomass (e.g., crops, waste) to supply the facility with.

Smaller-scale facilities closer to the biomass being processed by the system reduce transportation costs, and in certain cases, may allow ethanol to be produced economically where it could not be produced economically by large-scale facilities.

The bioethanol production facilities can have all or some of the equipment necessary for producing the desired product from biomass. The biomass used by the systems include any type of biomass. In certain embodiments, more conventional sources of biomass such as corn, sugar beets, grains, sugar cane, or whey is used as the starting material. In other embodiments, less conventional sources of biomass are used including agricultural waste, algae, waste, and human waste. In certain embodiments, the systems do not use corn, sugar beets, or sugarcane. In certain embodiments, the systems do use corn. In other embodiments, the system uses sugar beets or sugarcane. In certain embodiments, the system is designed to use a variety of different types of biomass as starting material. In other embodiments, the system is designed to use one type of biomass. In certain embodiments, various components may be switched interchanged to allow for different types of biomass as starting materials.

In certain embodiments, the systems includes processes and apparatuses for pre-processing the biomass. In certain embodiments, the biomass is sorted. In other embodiments, the biomass is cleaned. In other embodiments, the biomass is packaged. In certain embodiments, the biomass is compacted or compressed. In other embodiments, the biomass is liquefied. In other embodiments, the biomass is dehydrated. The pre-processing of the biomass may take place at the site of harvesting the biomass, before transportation of the biomass, during the transportation, during storage of the biomass, or at the site of the energy production. Any equipment and methods used to pre-process biomass for energy production may be used. In certain embodiments, the pre-processing means is considered to be part of the system.

The process of producing energy (e.g., ethanol, hydrocarbons, gasoline, natural gas, methane, biodiesel, and hydrogen gas), electricity, plastics, polymers, nutrients (human and animal), proteins, biomolecules, pharmaceuticals (human and veterinary; e.g., drugs and medicines), fertilizer, or other products from biomass can be broken down into several steps. The first involves grinding the biomass into a fine powder, chopping the biomass, shearing the biomass, or otherwise making the complex carbohydrates or other biomolecules in the biomass available for further processing. In certain embodiments, the resulting biomass is then mixed with water and optionally microorganisms (e.g., bacteria), algae, enzymes, acid, base, or chemical reagent. The mixture is then optionally heated in a cooker or other apparatus to facilitate the break-down of complex sugars (e.g., cellulose, starch) into fermentable, simpler sugars (e.g., glucose). This step may also facilitate the breakdown of other biomolecules or cellular structures such as lipids, protein, nucleic acids, steroids, natural products, cell wall, cell membrane, and intracellular membranes. The resulting mixture, commonly known as the mash, is then fermented with the addition of a microorganism such as yeast. In certain embodiments, other genetically engineered microorganisms are used in the fermentation process. The microorganisms may be particularly suitable for fermenting or converting the biomass used in the process into the desired product. The fermentation/conversion process is continued until most of the sugars or other starting materials in the fermentation have been converted to ethanol or other desired product. In certain embodiments, co-products such as carbon dioxide, proteins, polymers, nutrients, fertilizers, or biomolecules are produced during the process. These may be collected, purified, packaged, and/or sold. The ethanol or other desired product is then optionally separated from the liquid, solid waste, and side products. This is typically done by distillation; however, other means of separating or purifying can also be used (e.g. column chromatography, extraction, chromatography, and crystallization). The distilled ethanol or other liquid energy source may still contain water so the desired product is optionally dehydrated. In certain embodiments, the desired product (e.g., ethanol) is dehydrated by running it over a substance that absorbs the remaining water such as molecular sieves. Once the desired product (e.g., ethanol) is purified to the desired degree of purity and water is removed, the desired product, particularly ethanol, is optionally denatured making it unfit for human consumption. The denaturation process is performed by missing the purified ethanol with 1-5% of gasoline or other organic solvent (e.g., methanol, acetone, isopropanol, and hexanes). Any waste can be discarded. In certain embodiments, the resulting distillers grain is used as livestock feed or as a fertilizer. Carbon dioxide also is produced as a by-product in the fermentation process. The carbon dioxide may be collected and sold. Other products such as polymers, protein, lipids, or other biomolecules are side products may be collected, packaged, and/or sold.

In certain embodiments, for example, when bioethanol is being produced from biomass, the facility or a component thereof includes a fermenter and distillation apparatus. In other embodiments, the production facility or component thereof also includes a cooker. The facility may also include a mill for grinding the biomass into smaller particles. The facility may also contain equipment such as columns for further purifying and dehydrating the ethanol after distillation. In certain embodiments, the facility also includes containers and mixing equipment for denaturing the produced ethanol. In certain embodiments, the various equipment is interconnected using piping to easily transfer the product from one step into equipment for performing the next step. As needed, the various equipment used in the process is fitted with heating and cooling means.

The process begins with biomass. The biomass used by the system may be any biomass suitable for producing ethanol or any other desired product. In certain embodiments, the biomass is high starch or high sugar agricultural crops such as corn, sugar cane, sugar and beets. The facilities are particularly useful and economical in converting crops to bioethanol because they can arrive or be assembled at the site when the crops (or other biomass) are ready for processing and then leave or be disassembled when the crops (or other biomass) have been processed. In certain embodiments, the biomass includes materials that contain cellulose, hemicellulose, lignin, protein, starch, and/or sugar. In certain embodiments, the biomass include plant matter such as trees, shrubs, grasses, weeds, agricultural crops, and agricultural waste. In certain embodiments, the biomass includes aquatic biomass, for example plankton, aquatic plants, and algae. Aquatic biomass is particularly suitable for being processed by the production facilities that are transported on water. In certain embodiments, the biomass is municipal waste, waste paper, and yard waste. A production facility may routinely travel to a particular area to convert its waste to ethanol or another desired product, or the facility may be assembled at a particular site. In other embodiments, the biomass is human waste.

The initial phases of sizing, milling, chopping, cutting, shearing, washing, liquefication, and/or saccharification of the biomass are performed by the facility or components thereof in some embodiments. In other embodiments, these steps or some of these steps are not performed by the facility or components thereof.

In certain embodiments, the biomass is mechanically broken down. For example, in certain embodiments, the sizing, milling, chopping, cutting, shearing, washing, or other pre-processing of the biomass for fermentation or conversion is not performed by the facility or components thereof, and the resulting processed biomass (also known as the meal) is the starting material used by the facility or a component thereof. In certain embodiments, the facility or a component thereof processes the biomass to allow for microorganisms or chemical to act on the carbohydrates in the biomass. This may include breaking down cell membranes, breaking down cells walls, increasing the surface area, breaking down macrostructures in the biomass.

In certain embodiments, the biomass or cellulose in the biomass is texturized or opened up as described in U.S. Pat. Nos. 5,952,105; 5,973,035; 6,207,729; 6,258,876; 6,448,307; 7,074,918; each of which is incorporated herein by reference; and published U.S. patent applications 20050084671; 20050090577; 20050200050; each of which is incorporated herein by reference. This process opens up the fibers in the biomass for further processing by chemicals and microorganisms added to the processed biomass in subsequent steps. The process increases the surface area where microorganisms or chemicals can work.

Figure 2:
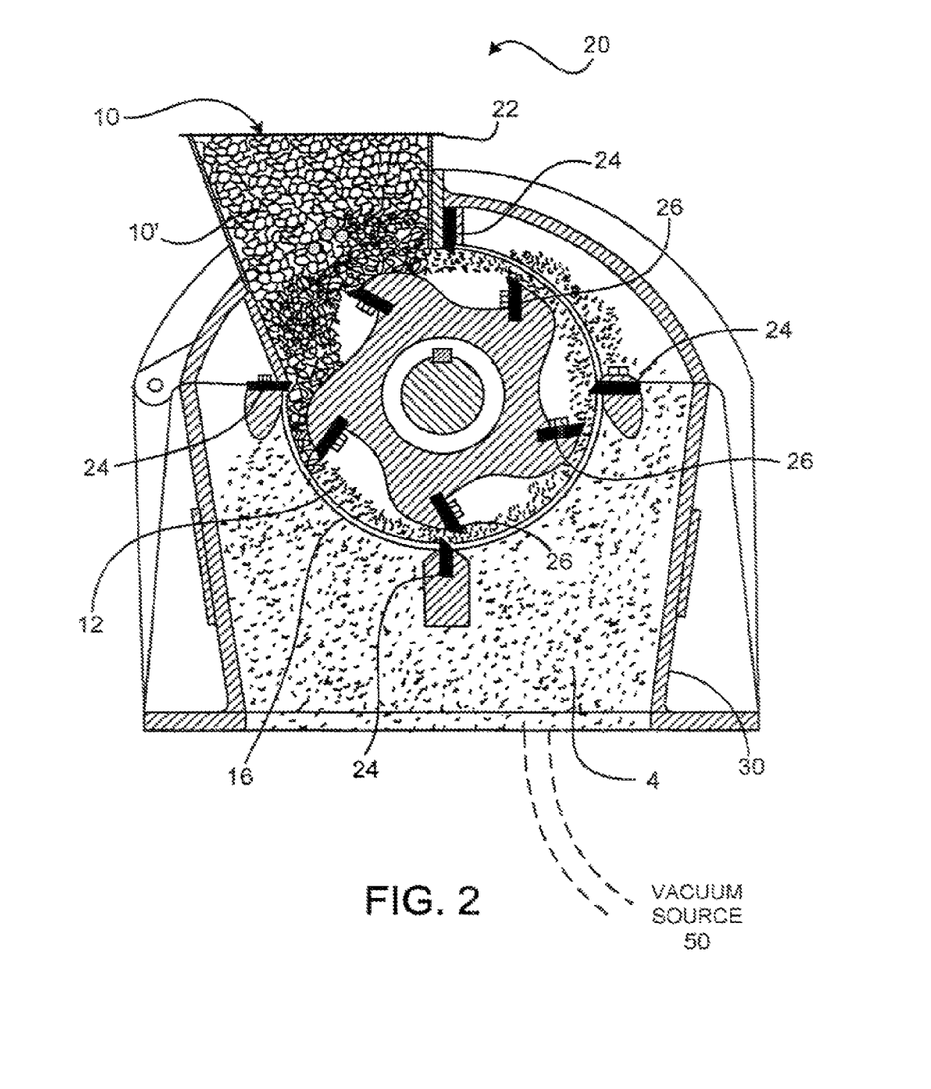
FIG. 2 is a cross-sectional view of a rotary knife cutter.

Referring to FIG. 2, a rotary knife cutter 20 includes a hopper 22 that can be loaded with a shredded fiber source 10' prepared by shredding fiber source 10. Shredded fiber source 10' is sheared between stationary blades 24 and rotating blades 26 to provide a first fibrous material 12. First fibrous material 12 passes through screen 16, and the resulting second fibrous material 4 is captured in bin 30. To aid in the collection of the second fibrous material 4, bin 30 can have a pressure below nominal atmospheric pressure, e.g., at least 10 percent below nominal atmospheric pressure, e.g., at least 25 percent below nominal atmospheric pressure, at least 50 percent below nominal atmospheric pressure, or at least 75 percent below nominal atmospheric pressure. In some embodiments, a vacuum source 50 is utilized to maintain the bin below nominal atmospheric pressure.

In certain embodiments, the biomass is mixed with water and optionally enzymes, microorganisms (e.g., bacteria, fungi, yeast), algae, other organisms, chemical reagents, or a combination thereof. This step breaks down the cellular structures, sugars, and biomolecules of the biomass before its conversion into the desired product. In certain embodiments, the biomass is mixed with a microorganism that aids in the breakdown of the biomass. The microorganism may be genetically engineered. In certain embodiments, the biomass is mixed with an algae that aids in the breakdown of the biomass. The resulting mixture may be heated, cooled, and mixed. to effect the desired changes to the biomass. In certain embodiments, the biomass is substantially liquefied resulting in a mash before it is transferred to the facility or a component thereof. In still other embodiments, the complex sugars in the mash are broken down into simpler, fermentable sugars, and the resulting mash is transferred to the facility or a component thereof for processing.

Once the biomass or a processed form of the biomass (e.g., the meal, the mash, opened and fiber) enters the facility or component thereof, it is further processed to form ethanol or any other desired product. In certain embodiments, the facility or a component pre-processes, liquefies, and converts the complex sugars in the mash to simpler sugars. In other embodiments the facility or a component thereof liquefies and converts the complex sugars to simpler sugars for distillation. In still other embodiments, the complex sugar in the mash are converted to simpler sugars in the facility or a component thereof. This conversion process is effected by enzymes such as amylase or cellulase, acid (e.g., sulfuric acid), microorganisms, and/or heat. The conversion process breaks down complex sugars such as cellulose and starch to simpler 5- or 6-carbon sugars such as glucose.

Once the mash with the broken down sugars is obtained either through processing inside or outside the facility, the fermentation/conversion process is begun. In certain embodiments, the mash is fermented to produce ethanol. The fermentation process is typically begun by bringing the mash to a particular temperature, for example, between 30 and 45° C. In certain embodiments, the fermentation takes place at approximately 30° C. In certain embodiments, the pH of the mash is adjusted to approximately pH 6-8, preferably approximately pH 7-7.5. In certain embodiments, the fermentation is carried out in an oxygen-depleted atmosphere. A fermenting microorganism is then added to the mash. In certain embodiments, the fermenting microorganism is yeast. In other embodiments, the fermenting microorganism is *Saccharomyces cerevisiae*. In certain embodiments, the fermenting organism is *Schizosaccharomyces pombe*. In other embodiments, the microorganism is *Zymomonas mobilis*. In other embodiments, the microorganism is *Escherichia coli*. In certain embodiments, the microorganism is a genetically engineered organism. Examples of genetically engineered fermenting organisms useful in the production of bioethanol are described in U.S. Pat. Nos. 6,699,696; 6,306,639; 5,162,516; 5,028,539; 5,000,000; 4,400,470; each of which is incorporated herein by reference. In certain embodiments, the fermentation mixture is kept at a constant temperature and pH during the fermentation process. The fermentation typically last from 24 hours to 500 hours. In certain embodiments, the fermentation lasts from 50-200 hours. In certain other embodiments, the fermentation last from 100-200 hours. As would be appreciated by one of skill in this art, the biomass, microorganism, temperature, and other conditions used in the fermentation will determine the length of time needed to convert the biomass to ethanol.

In other embodiments, the processed biomass or mash is converted into another energy source besides ethanol (e.g., gasoline, hydrocarbons, hydrogen gas, natural gas, bio-diesel, and electricity) or another desired product or co-product. This conversion is effected by microorganisms. In certain embodiments, the microorganisms are genetically engineered. In certain particular embodiments, the microorganisms are genetically engineered to produced the desired product. For example, in certain embodiments, the microorganisms are designed to produce natural gas or hydrogen gas from biomass. In other embodiments, the microorganisms are designed to produce gasoline or hydrocarbons from biomass.

In other embodiments, the processed biomass or mash is converted into other desired products such as plastics, polymers, and nutrients. This conversion is effected by microorganisms. In certain embodiments, the microorganisms are genetically engineered. In certain particular embodiments, the microorganisms are genetically engineered to produced the desired polymer. In certain embodiments, the microorganisms are designed to produce nutrients.

In certain embodiments, the desired product is removed as it is produced. In other embodiments, the desired product is purified from the fermentation/conversion after the fermentation/conversion is stopped. In the production of bioethanol, after the fermentation step is complete, the fermented mash (also known as beer) contains anywhere from 5% to 20% ethanol. In some embodiments, the ethanol is removed as it is produced. The ethanol is purified from the water, and solids by distillation. The distillation process involves vaporizing the ethanol and then recondensing it into liquid form again. The purity of the ethanol obtained from the distillation can be increased by repeatedly distilling the resulting ethanol until the desired purity is achieved. The ethanol may be further purified by removing any remaining water using a dehydration step. In certain embodiments, the ethanol is passed over a material which absorbs water such as molecular sieves. In certain embodiments, the ethanol is distilled or azeotroped to remove most of the water from the ethanol. Similarly, if a different desired product is produced than ethanol, it can similarly be purified from the converted biomass. Preferably, as much of the desired product is produced before the conversion process is stopped. In certain embodiments, the desired product is drawn off as it is produced.

Analogously, the facilities may produce 100% ethanol or ethanol of any desired state of purity. For example, the facility with its distillation apparatus may produce less than 100% pure ethanol. In certain embodiments, the ethanol is at least 80%, at least 90%, at least 95%, at least 98%, or at least 99% pure. The ethanol, if desired, can then be further purified and/or dehydrated outside the mobile facility. In certain embodiments, the facility produces pure ethanol that is subsequently denatured. An organic solvent such as methanol, isopropanol, hexanes, and gasoline. is added to the purified ethanol to produced denatured ethanol, which is unfit for human consumption. Exemplary denaturants include methanol, camphor, aldehydes, amyl alcohol, gasoline, isopropanol, terpineol, benzene, castor oil, acetone, nicotine, acids, kerosene, and diethyl phthalate. In certain embodiments, 1-10% of organic solvent is added to the ethanol. In other embodiments, 1-5% of organic solvent is added. In certain embodiments, 2-5% of gasoline is added to the ethanol to denture it.

Any of the knowledge in the art of producing of ethanol from biomass may be used in the system for producing ethanol. Various aspects of the process of producing ethanol from biomass are described in U.S. Pat. Nos. 7,070,967; 7,037,704; 7,037,378; 7,033,781; 7,026,152; 7,022,894; 6,933,404; 6,927,048; 6,908,995; 6,861,248; 6,849,434; 6,846,657; 6,803,218; 6,755,975; 6,737,257; 6,716,631; 6,703,227; 6,699,696; 6,663,780; 6,660,506; 6,648,930; 6,605,376; 6,596,908; 6,592,921; 6,582,944; 6,555,350; 6,528,311; 6,509,180; 6,468,567; 6,420,146; 6,387,554; 6,379,964; 6,372,269; 6,355,456; 6,352,859; 6,335,198; 6,335,177; 6,333,181; 6,326,204; 6,306,639; 6,287,862; 6,280,986; 6,267,309; 6,251,674; 6,224,915; 6,136,577; 6,130,076; 6,107,093; 6,090,595; 6,054,611; 6,045,660; 6,001,568; 5,981,807; 5,975,439; 5,958,698; 5,932,456; 5,916,787; 5,916,780; 5,892,107; 5,882,905; 5,869,301; 5,840,971; 5,821,093; 5,789,210; 5,779,164; 5,756,862; 5,735,916; 5,705,369; 5,677,154; 5,616,478; 5,609,723; 5,578,472; 5,571,703; 5,559,031; 5,554,520; 5,545,543; 5,504,259; 5,503,996; 5,488,185; 5,487,989; 5,482,846; 5,474,924; 5,470,433; 5,424,417; 5,424,202; 5,407,817; 5,397,436; 5,372,939; 5,345,477; 5,258,293; 5,231,017; 5,223,567; 5,186,722; 5,182,199; 5,135,861; 5,134,944; 5,106,634; 5,100,791; 5,086,144; 5,081,285; 5,071,675; 5,063,156; 5,061,497; 5,047,332; 5,028,539; 5,013,436; 5,000,000; 4,985,355; 4,952,504; 4,952,503; 4,933,198; 4,886,751; 4,885,241; 4,859,758; 4,840,903; 4,840,902; 4,830,964; 4,816,407; 4,816,399; 4,812,410; 4,808,527; 4,808,526; 4,790,238; 4,778,688; 4,769,324; 4,746,615; 4,746,610; 4,731,329; 4,661,643; 4,650,689; 4,647,534; 4,628,031; 4,612,286; 4,604,352; 4,567,145; 4,560,659; 4,556,744; 4,541,897; 4,523,928; 4,522,920; 4,517,298; 4,510,242; 4,507,505; 4,490,469; 4,490,468; 4,480,090; 4,454,358; 4,451,597; 4,447,534; 4,443,637; 4,443,544; 4,443,543; 4,442,210; 4,421,939; 4,413,058; 4,409,405; 4,405,815; 4,403,034; 4,400,551; 4,400,470; 4,400,469; 4,395,488; 4,393,136; 4,386,009; 4,372,822; 4,358,536; 4,357,480; 4,356,262; 4,355,192; 4,355,108; 4,346,113; 4,335,207; 4,333,852; 4,328,375; 4,326,036; 4,321,141; 4,317,884; 4,302,357; 4,301,312; 4,301,253; 4,287,303; 4,273,621; 4,262,154; 4,255,300; 4,253,987; 4,233,466; 4,220,803; 4,168,391; 4,164,445; 4,139,509; 4,134,926; 4,094,742; each of which is incorporated herein by reference; and published U.S. patent applications, Ser. No. 20060154844; 20060154353; 20060154342; 20060143728; 20060141594; 20060141584; 20060134747; 20060121589; 20060121581; 20060115779; 20060110812; 20060110810; 20060105443; 20060105442; 20060105440; 20060101540; 20060094080; 20060088922; 20060084156; 20060073220; 20060064786; 20060057692; 20060057691; 20060051847; 20060043020; 20060035353; 20060035346; 20060026715; 20060019400; 20060019360; 20060014841; 20060014260; 20060013765; 20060009537; 20060003408; 20050289670; 20050272134; 20050266543; 20050266540; 20050266105; 20050266100; 20050260554; 20050250192; 20050244934; 20050244878; 20050233031; 20050226950; 20050214915; 20050214913; 20050214911; 20050214408; 20050198704; 20050181492; 20050176974; 20050170483; 20050158836; 20050142250; 20050136525; 20050136520; 20050124010; 20050115904; 20050115897; 20050112739; 20050109697; 20050107482; 20050106657; 20050100996; 20050074865; 20050069998; 20050069598; 20050065446; 20050064052; 20050061313; 20050056600; 20050055874; 20050033045; 20050031719; 20050026261; 20050019932; 20050013901; 20050003025; 20040262161; 20040261145; 20040253713; 20040231661; 20040229321; 20040225164; 20040204503; 20040197890; 20040194161; 20040191375; 20040185543; 20040185542; 20040152159; 20040121436; 20040116757; 20040108085; 20040102619; 20040094144; 20040091983; 20040087808; 20040082044; 20040081648; 20040081647; 20040077090; 20040067550; 20040060868; 20040060673; 20040058052; 20040055041; 20040047799; 20040044087; 20040029238; 20040011258; 20040000521; 20030236311; 20030235881; 20030222021; 20030219512; 20030211585; 20030204988; 20030199072; 20030199049; 20030194788; 20030186402; 20030180900; 20030175903; 20030170861; 20030170330; 20030166179; 20030162851; 20030162271; 20030157675; 20030153059; 20030148309; 20030143704; 20030119006; 20030115792; 20030114330; 20030113735; 20030113734; 20030113732; 20030100807; 20030094416; 20030087381; 20030077771; 20030072822; 20030068415; 20030054535; 20030054500; 20030049867; 20030046724; 20030044499; 20030044495; 20030041982; 20030019736; 20030018063; 20030008363; 20030008362; 20030006191; 20021097686; 20020197688; 20020193617; 20020192774; 20020188965; 20020188459; 20020164731; 20020164730; 20020160469; 20020159990; 20020155583; 20020153317; 20020142410; 20020132350; 20020104518; 20020094575; 20020091165; 20020081677; 20020069987; 20020062594; 20020061561; 20020055135; 20020042111; 20020037564; 20020034816; 20020026744; 20020023278; 20020015871; 20010024796; 20010023034; 20010006795; each of which is incorporated herein by reference.

Other Embodiments

A number of embodiments of the invention have been described. Nevertheless, it will be understood that various modifications may be made without departing from the spirit and scope of the invention. Accordingly, other embodiments are within the scope of the following claims.

What I claim is:

1. A method of producing products from cellulosic and/or lignocellulosic biomass, comprising:
    assembling, at a first site, a portable apparatus comprising (a) a mechanical treatment module and (b) a fermenter, reactor or converters;
    utilizing the mechanical treatment module to open up and/or texturize said biomass at the first site to make complex carbohydrates or other biomolecules available for further processing;
    contacting said opened up and/or texturized biomass with one or more microorganisms in the fermenter, reactor or converter to produce a first product;
    isolating the first product;
    transporting said apparatus to a second site;
    utilizing the mechanical treatment module to open up and/or texturize biomass at the second site to make complex carbohydrates or other biomolecules available for further processing;
    contacting said opened up and/or texturized biomass at the second site with one or more microorganisms in the fermenter, reactor or converter to produce a second product;
    isolating the second product;
    wherein both the first product and the second product are selected from the group consisting of nucleic acids, steroids, nucleotides, nucleosides, amino acids, energy sources, alcohols, hydrocarbons, hydrogen, natural gas, biodiesel, electricity or combinations thereof.

2. The method of claim 1, wherein the biomass is selected from the group consisting of sugar cane, shrubs, grasses, seaweed, corn husks, bushes, lumber, wood waste, pulp, leaves, twigs, plant cuttings, branches, trees, vines, sewage, agricultural waste, and mixtures thereof.

3. The method of claim 1, wherein transporting is performed with a nautical vessel.

4. The method of claim 3, wherein the nautical vessel is a boat, a barge, a ship, a dock, a floating platform, a sea platform, or a sea rig.

5. The method of claim 1, wherein transporting is performed with a land vehicle.

6. The method of claim 5, wherein the land vehicle is a car, truck, tractor trailer or train.

7. The method of claim 1, wherein the transporting is performed by a land vehicle and a water vehicle.

8. The method of claim 1, said mechanical treatment module is selected from the group consisting of cutters, shearing devices, and mills.

9. The method claim 1, wherein the first site and second site are spaced apart by a distance of about 25 miles or more.

10. The method of claim 1, wherein the first site and second site are spaced apart by a distance of about 100 miles or more.

11. The method of claim 1, wherein producing the first product and producing the second product comprises utilizing the fermenter to hydrolyze the lignocellulosic biomass, and then ferment the sugars obtained from hydrolysis.

12. The method of claim 1, further comprising transporting the apparatus to a third site, and then producing a third product at the third site,
    wherein the third product is selected from the group consisting of energy sources, alcohols, hydrocarbons, hydrogen, natural gas, biodiesel, electricity or combinations thereof.

13. The method of claim 12, further comprising transporting the fermenter to a fourth site, and then producing a fourth product at the fourth site,
    wherein the fourth product is selected from the group consisting of energy sources, alcohols, hydrocarbons, hydrogen, natural gas, biodiesel, electricity or combinations thereof.

14. The method of claim 1, wherein the one or more microorganisms comprises one or more genetically engineered bacteria.

15. The method of claim 1, wherein the mechanical treatment module is a cutter and/or shearing device.

* * * * *